US00PP18489P3

(12) United States Plant Patent
Cox et al.

(10) Patent No.: US PP18,489 P3
(45) Date of Patent: Feb. 19, 2008

(54) **'LITTLE HONEY': A *GREVILLEA* CULTIVAR**

(50) Latin Name: *Grevillea*
Varietal Denomination: Little Honey

(75) Inventors: Denis Eric Cox, Queensland (AU); Janice Evelyn Glazebrook, Queensland (AU)

(73) Assignees: James Walter Carter, Queensland (AU); Elva Lorraine Carter, Queensland (AU)

( * ) Notice: Subject to any disclaimer, the term of this patent is extended or adjusted under 35 U.S.C. 154(b) by 0 days.

(21) Appl. No.: 11/118,736

(22) Filed: Apr. 29, 2005

(65) Prior Publication Data

US 2006/0248620 P1 Nov. 2, 2006

(51) Int. Cl.
*A01H 5/00* (2006.01)

(52) U.S. Cl. ..... Plt./226

(58) Field of Classification Search ..... Plt./226
See application file for complete search history.

(56) References Cited

PUBLICATIONS

UPOV–ROM GTITM, Plant Variety Database, 2003/05, GTI Jouve Retrieval Software, Citation for grecillea 'Little Honey'.*
Australia Plant Varieties Journal, 2005, vol. 18, Number 3; pp. 85–89. (6 pages total).*
Internet website: www.carterstubes.com.au/index.php?p=little_honey (1 page total).*
Australian Plant Varieties Journal, 2003, Quarter Two, vol. 16, No. 2, pp.9 and 14. (3 pages total).*

* cited by examiner

*Primary Examiner*—Kent Bell
*Assistant Examiner*—S. B. McCormick-Ewoldt
(74) *Attorney, Agent, or Firm*—Saliwanchik, Lloyd & Saliwanchik

(57) ABSTRACT

A new and distinct plant, a cultivar of *Grevillea,* named *Grevillea* sp. 'Little Honey,' is provided.

7 Drawing Sheets

FIELD OF THE INVENTION

A new distinct cultivar of *Grevillea,* named *Grevillea* sp. 'Little Honey,' is provided.

*Grevillea* shrubs and trees come from Australia and are grown for their beautiful fern-like foliage and small tubular flowers. They can grow outside in mild climates such as California. The flowers of these plants grow in clusters at the ends of the branches. They are about half of an inch long and typically come in reds, yellows, or pinks.

The plant of the subject invention is characterized by its orange flowers, orange styles, and fine leaves with creamy-silvery undersides.

*Grevillea* sp. 'Little Honey' looks fantastic in a pot, makes an ideal landscaping plant and is suitable for all size gardens from the biggest to the smallest.

BACKGROUND OF INVENTION

A new seedling arose in a Burpengary, QLD garden bed of Dennis Cox and Janice Glazebrook in 1990. The seedling came up in this garden near a plant of *Grevillea* sp. 'Honey Gem' (not patented), which is itself a cultivar, *Grevillea banksii*×*Grevillea pteridifolia,* and *Grevillea* 'Banksii' (white dwarf form) (not patented). They are the suspected parent cultivars. The seed parent *Grevillea* sp. 'Honey Gem' is characterized by orange colored flower, orange style, broader leaves with yellowish undersides, and larger plant height (6 m). The pollen parent *Grevillea* 'Banksii' is characterized by cream colored flower, cream style, and more lobed silvery leaves. The new plant was grown by cuttings for three generations. This plant was selected because of its smaller growth form and profuse flowering.

BRIEF DESCRIPTION OF THE PHOTOGRAPHS

Figure 1:
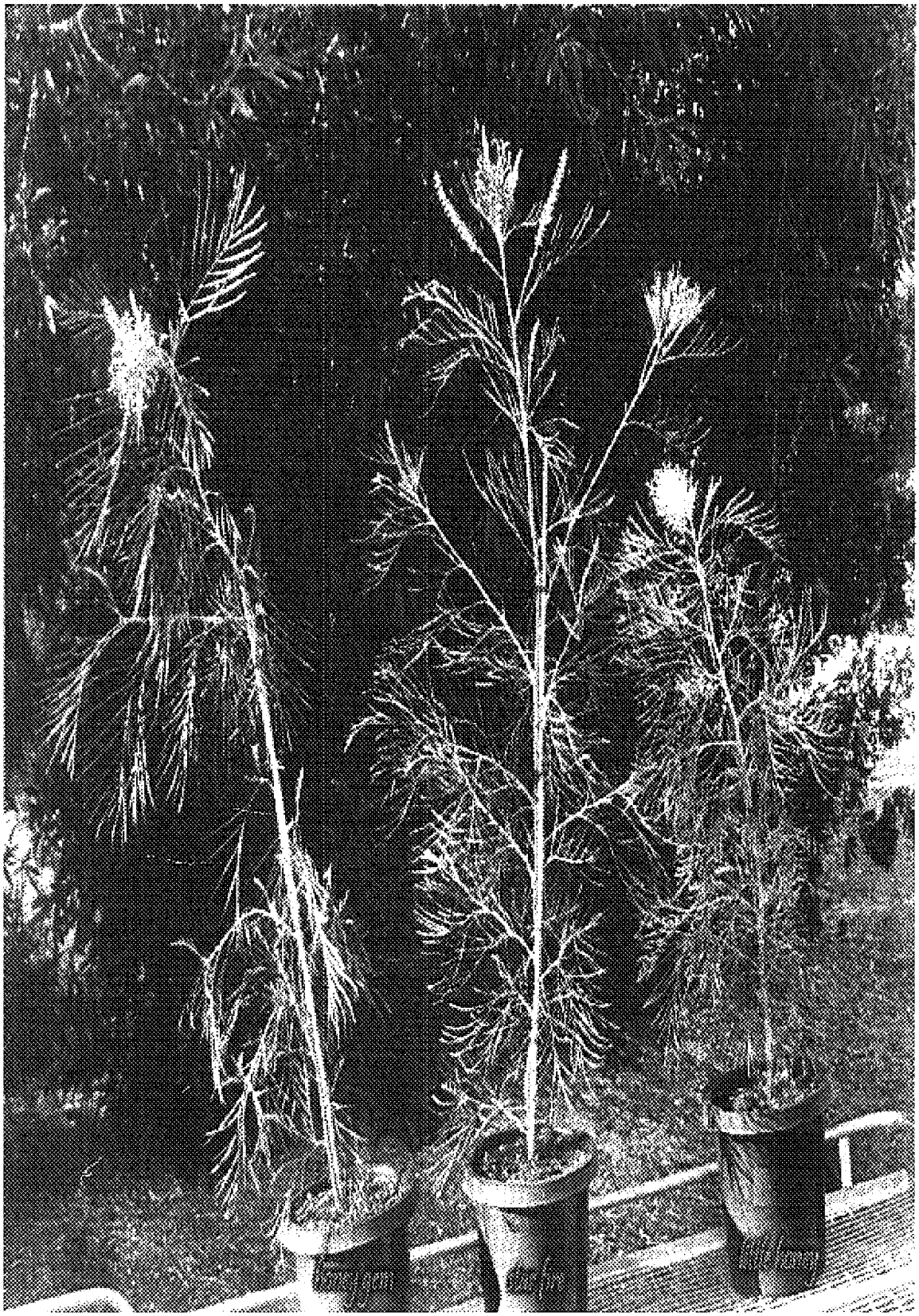

FIG. 1 Photograph comparing three different types of *Grevillea* sp.: 'Honey Gem', 'Star Fire', and 'Little Honey'.

Figure 2:
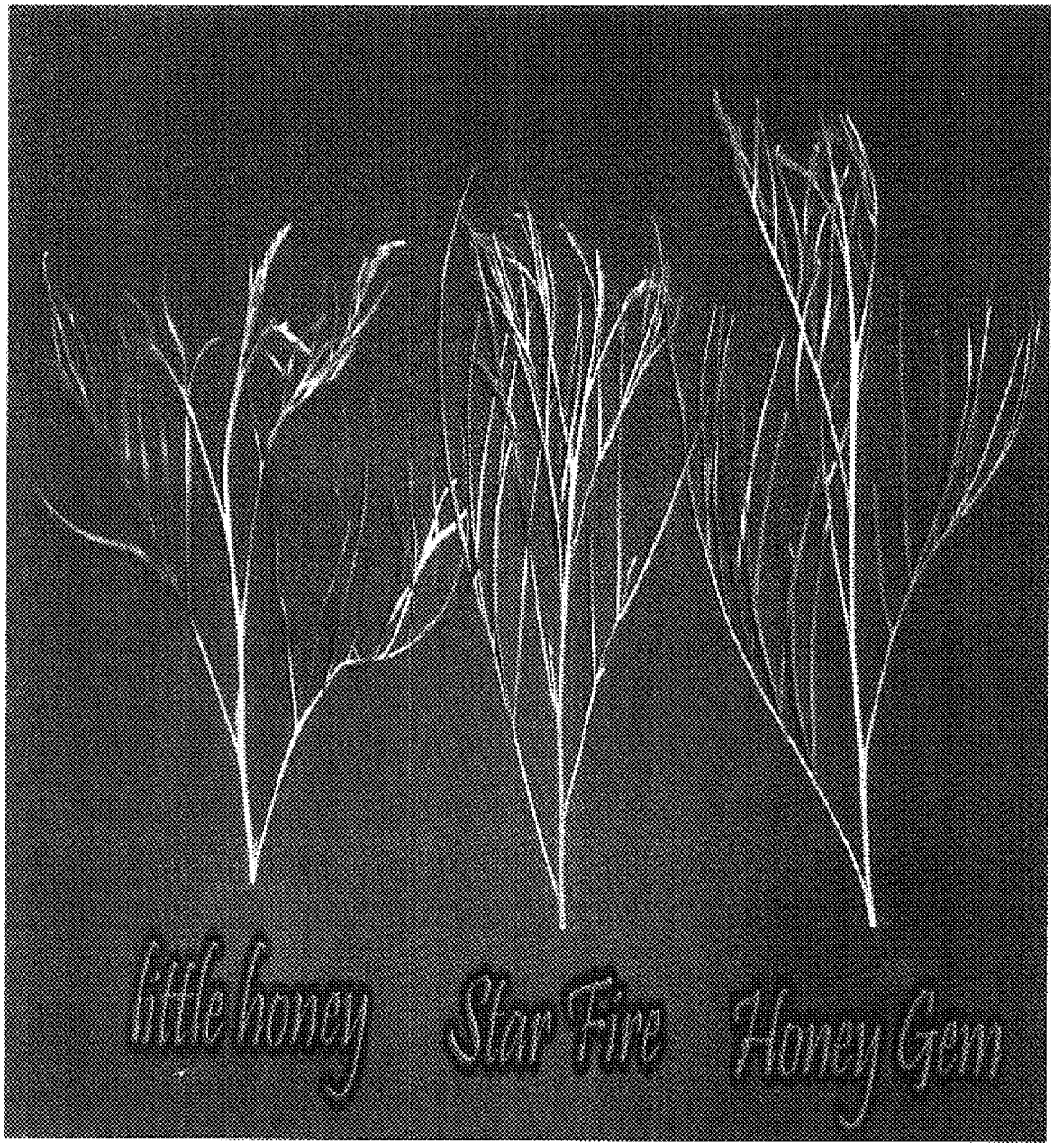

FIG. 2 Photograph comparing three different types of *Grevillea* sp.; 'Honey Gem', 'Star Fire', and 'Little Honey'. This photograph is a view of the typical leaves of each cultivar.

Figure 3:
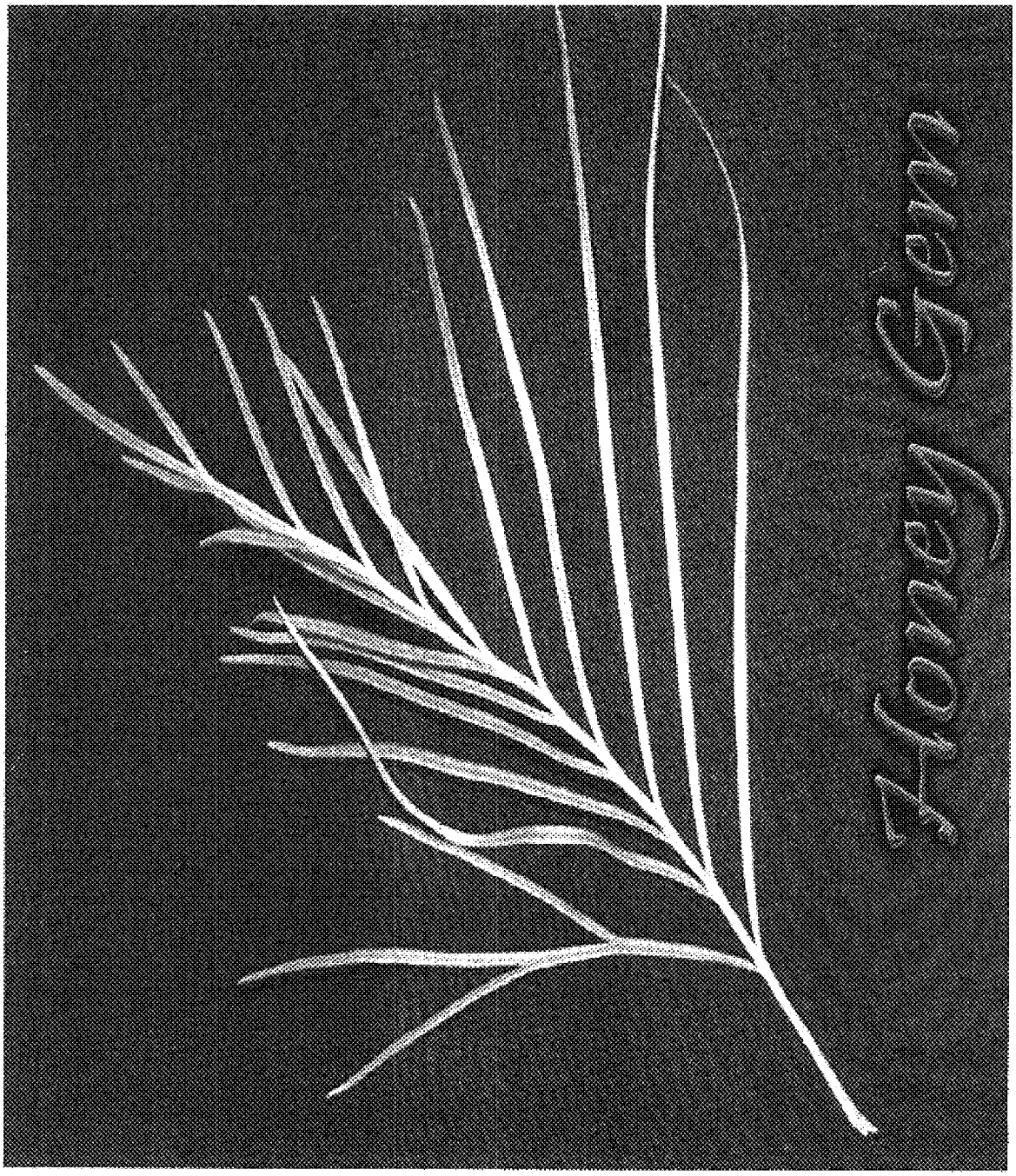

FIG. 3 Close up photograph showing the typical leaves of 'Honey Gem'.

Figure 4:
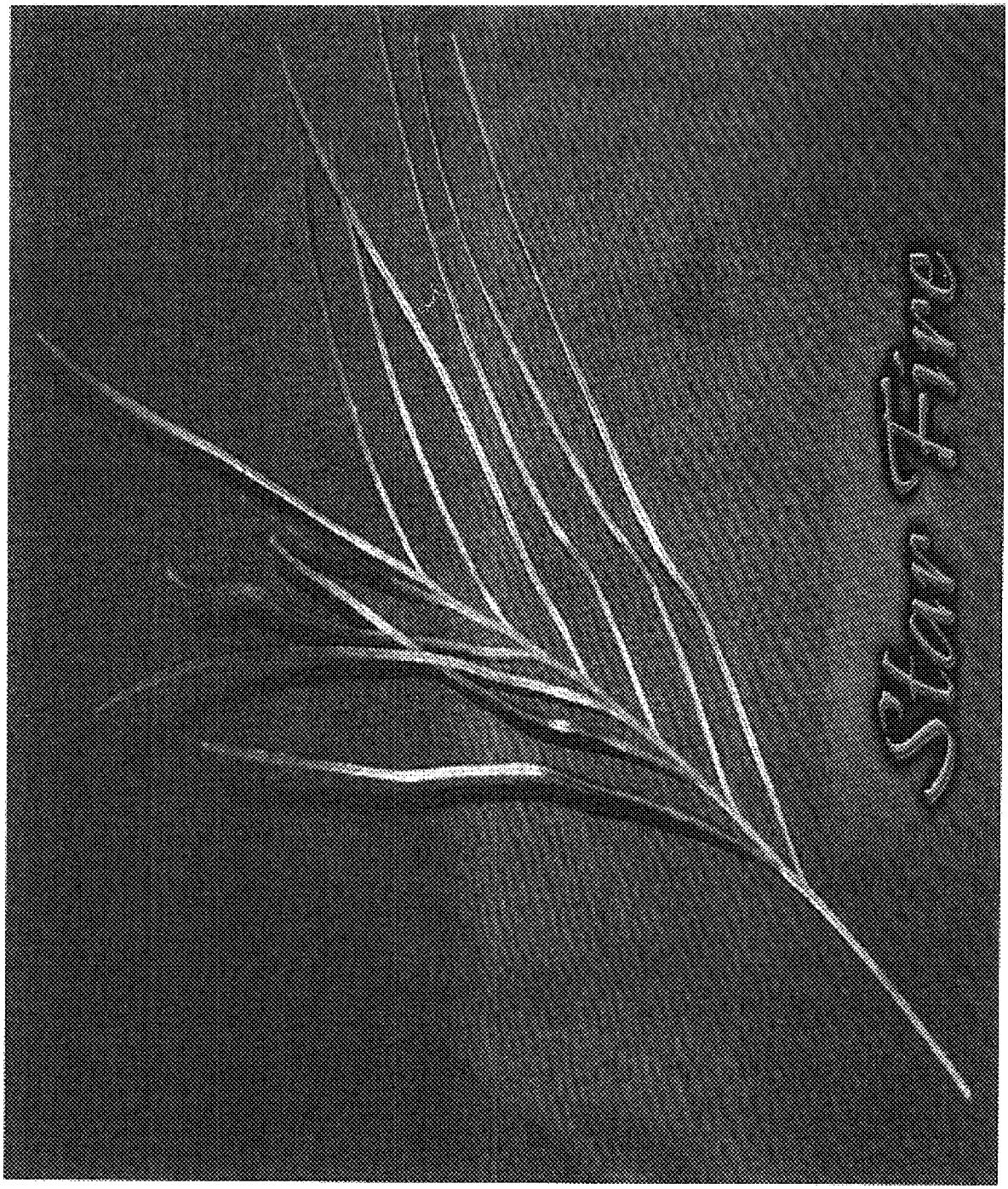

FIG. 4 Close up photograph showing the typical leaves of 'Star Fire'.

Figure 5:
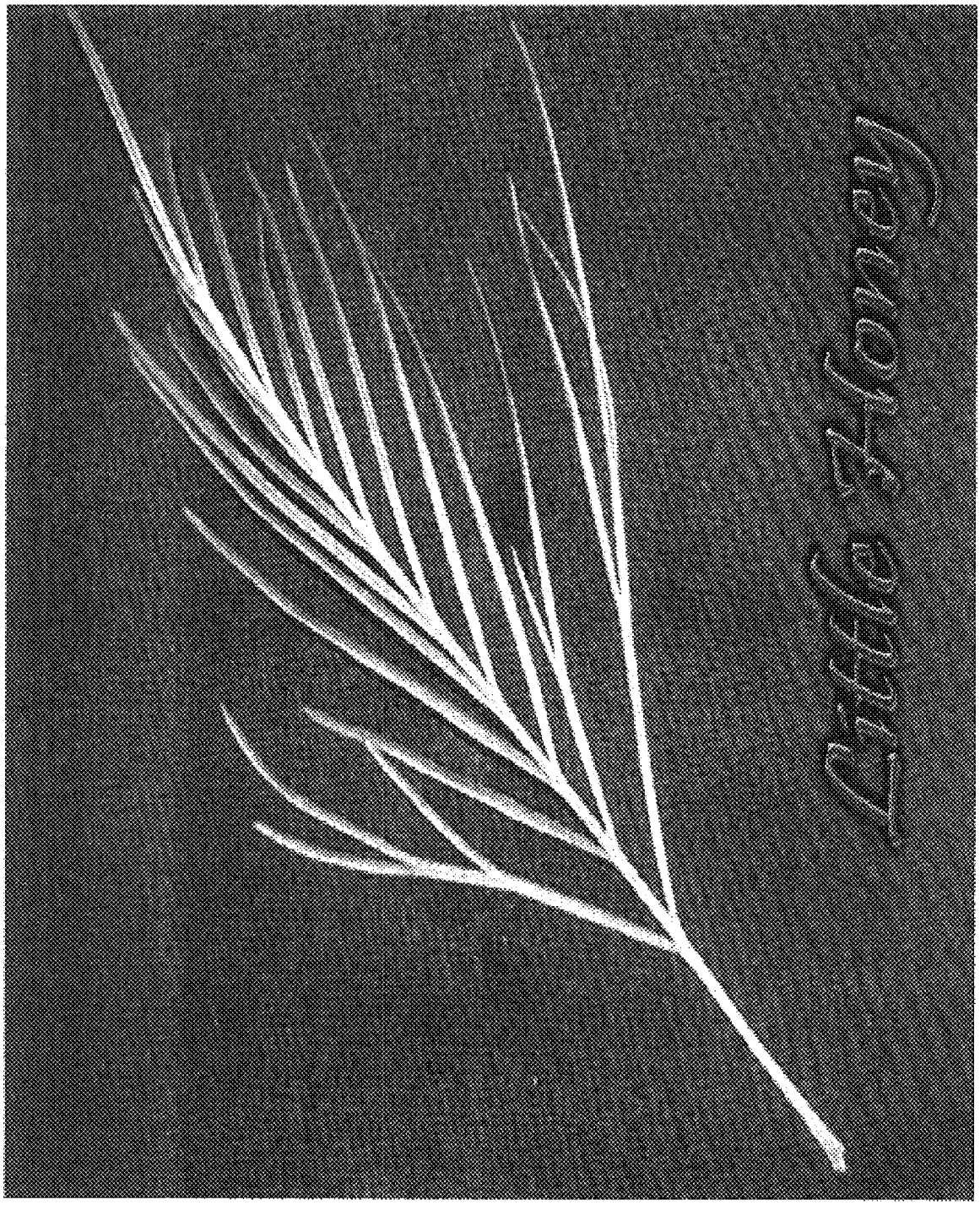

FIG. 5 Close up photograph showing the typical leaves of 'Little Honey'.

Figure 6:
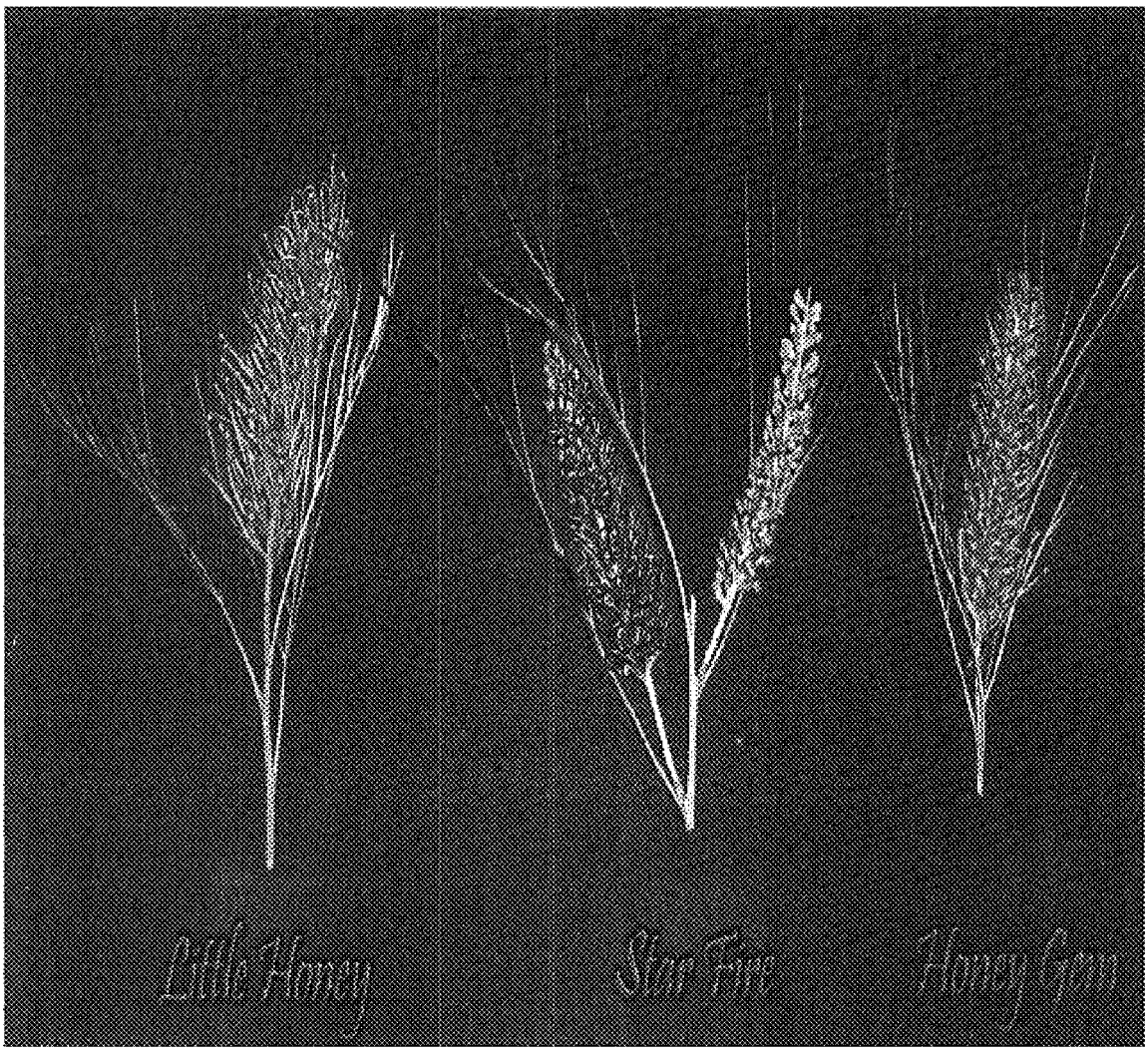

FIG. 6 Photograph comparing three different types of *Grevillea* sp.; 'Honey Gem', 'Star Fire', and 'Little Honey'. This photograph is a view of the typical blooms of each cultivar.

Figure 7:
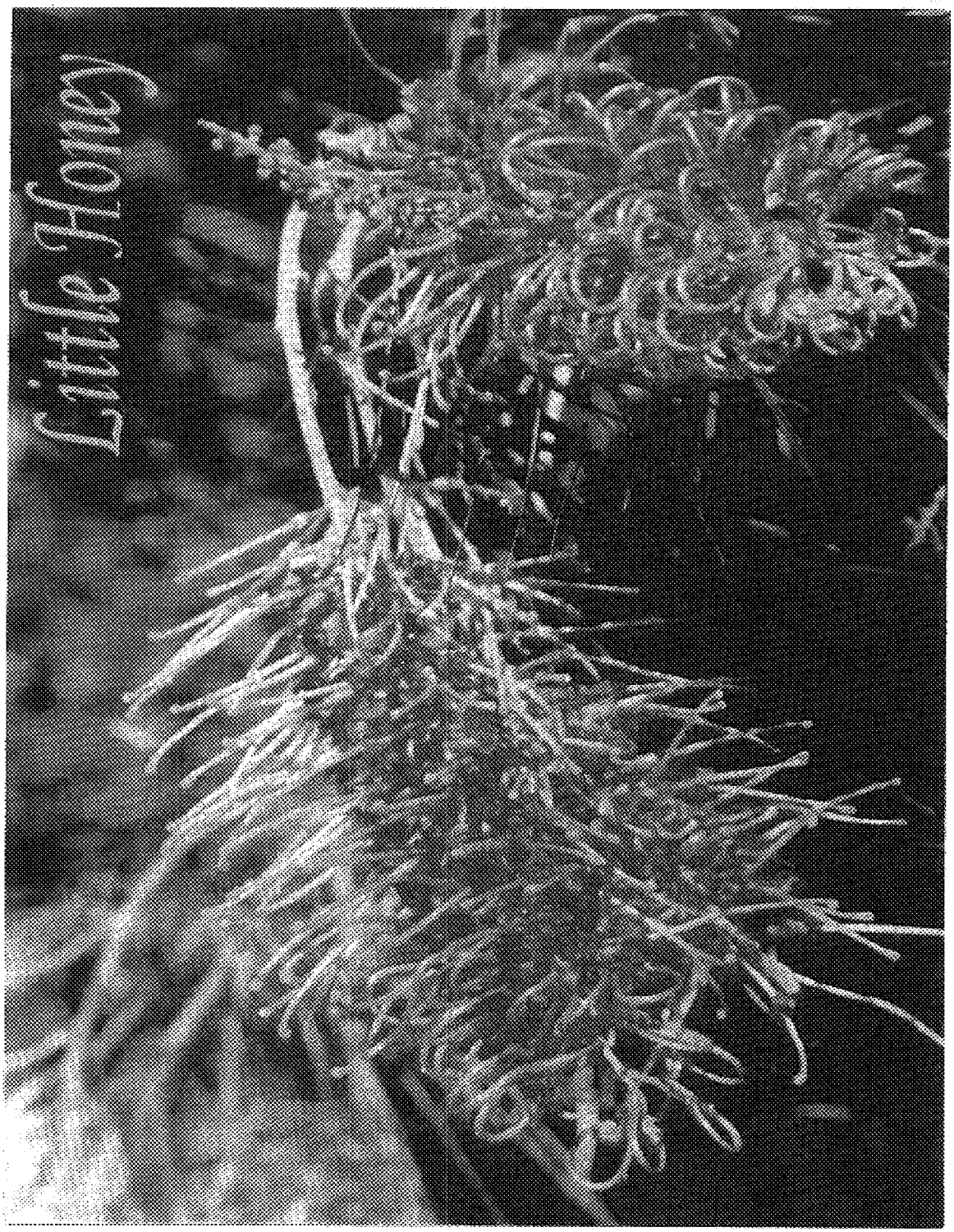

FIG. 7 Close up photograph of the typical blooms of 'Little Honey'.

DETAILED DESCRIPTION OF THE NEW VARIETY

*Grevillea* sp. 'Little Honey' arose in a Burpengary, QLD garden bed of Dennis Cox and Janice Glazebrook in 1990. The 'Little Honey' seedling came up in a garden near a plant of *Grevillea* sp. 'Honey Gem' and *Grevillea* 'Banksii' (white dwarf form). In 1989, the breeders took cuttings off their plant in 1989 and struck (propagated) them. Numbers of cutting were very small in size. These struck cuttings were potted up in larger pots, planted in 1990 and grown for two years and cuttings taken from them. This process was repeated to three generations. These potted up cuttings were then planted in garden beds on the breeders' property to ensure plant growth, height and shape were all consistent and that the flowering periods and flower color were consistent for all generations.

The time required to initiate root development of 'Little Honey' in the propagation tube is dependent on both the time of the year the cutting is taken and the hardness of the material taken, in the range of three to six months. Then, the root-letted cuttings are sun-hardened for further root development, approximately six to eight weeks still in tube. The rooted cuttings are then potted up into a smaller pot another five to six months in warm conditions (longer period if climactic conditions are cooler). Compared to other *Grevillea* hybrids, including *Grevillea* sp. 'Honey Gem', *Grevillea* sp. 'Little Honey' has a smaller, finer, and much slower root system. These aspects make the cultivar ideal for either large pots or confined spaces.

This plant is advantageous in at least the following aspects:

- Its attractive foliage
- Its unique pale flowers
- Nicely-shaped shrub
- Profuse flowering

*Grevillea* sp. 'Little Honey' is distinctively different from other known *Grevillea* cultivars. For example, a close variety of *Grevillea* sp. 'Little Honey' is *Grevillea* 'Star Fire', which is different from 'Little Honey' by plant height, flower color, and foliage. Table 1 presents a comparison of *Grevillea* sp. 'Little Honey' with the most similar varieties of *Grevillea,* which were used by the breeders as comparator plants for the growing trials.

TABLE 1

| Name of Closest Variety | Comparator variety is different by: | Distinctive characters of 'Little Honey' | Comparator variety characters |
|---|---|---|---|
| Maternal Parent *Grevillea* 'Honey Gem' | Plant height; flower color; leaf color; leaf size. | 2 m high; orange flowers; yellow styles; leaves creamy, silvery on the underside; leaves are finer. | 6 m high; orange flowers; orange styles; leaves yellowish on the underside; leaves broader. |
| Other Parent *G. Banksii* white low or prostrate form | Flower color; foliage | Orange flower; yellow style; fine, long, thin leaves. | Cream flower; cream style; more lobed and silvery in color. |
| Closest Variety *Grevillea* 'Honey Gem' | Plant height; flower color; leaf color; leaf size. | 2 m high; orange flowers; yellow style; fine, long leaves that are silvery on the underside. | 6 m high; orange flowers; orange style; broader, longer leaves; leaves yellowish on the underside. |
| Other Closest Variety *Grevillea* 'Star Fire' | Plant height; flower color; foliage. | 2 m high; orange flowers; yellow styles; long, fine leaves that are silvery on the underside. | 2.5 m to 3 m high; coppery brown aging to red with pink styles and yellow tip; leaves not as broad; leaves not as long. |

DETAILED BOTANICAL DESCRIPTION

The following observations, measurements and comparisons describe the cultivar grown in Burpengary, QLD in open conditions on a gravel bed. Tube stock of each variety was planted into 200 mm pots of standard bark potting mix. The age of the observed plants is two years old.

The following description uses color references to The Royal Horticultural Society Color Chart (1986), except where general terms of ordinary dictionary significance are used.

Botanical classification: *Grevillea* hybrid cultivar *Grevillea* sp. 'Little Honey'.

Parentage: *Grevillea* sp. 'Honey Gem' and *Grevillea* 'Banksii' (white dwarf form).

Propagation: 'Little Honey' needs to be reproduced from a cutting to maintain the unique characteristics such as flower, foliage, shape and size.

Plant description:

*Plant size.*—Average height attained about 2 m: medium; habit: sparse to medium bushy shrub; average width about 1.5 m.

*Stem.*—Coloration: green (RHS 117B); texture: pubescence strong (hairiness). The exact stem diameter was not recorded by the breeder, as recordation of the stem diameter was not required under the breeders' citizenship country's laws at the time of breeding. However, the illustrated variety and comparators had a stem diameter of about 10-13 mm.

*Leaf.*—Mean length: 222.8 mm; mean width: 160.0 mm; mean lobe width: 2.50 mm; degree of division: deep; variegation: absent; color of lower side of leaf: green (RHS 139A); color of upper side of leaf: greyed green (RHS 190A); margin: smoothly revolute to the mid vein, lower surface enclosed; apex: pointed, very narrow to narrow; base: 15 cm; texture: degree of hairiness on upperside — very weak to weak, degree of hairiness on lowerside — weak; arrangement: parallel lobes; leaflet mean length: 250.6 mm; leaflet mean width: 159.3 mm.

*Inflorescence.*—Form: cylindrical; position: terminal or at end of lateral stems; length: long, about 160 mm; attitude: semi-erect; density of florets: dense, about 85 florets per inflorescence; width: medium, about 85 mm.

*Florets.*—Length: 41.1 mm (tube length (mean 8.8 mm) plus the style length (mean 32.3 mm)); color: RHS 34C, RHS 24D, and RHS 6B.

*Pedicel.*—Length: very short to short, about 10 mm; attitude: leaning away from inflorescence peduncle.

*Perianth.*—Color: RHS 34C; length; short, about 15 mm; pubescence: present; overall degree of pubescence: medium.

*Style.*—Color: orange (RHS 24D); length: short, about 32 mm.

*Pollen presenter* (*located at the tip of the style and holds pollen*).—Color: yellow (RHS 6B); shape: dome-like.

*Ovary.*—Pubescence: present; degree of pubescence: strong.

*Ovules.*—No seeds have been found.

*Reproduction.*—Cultivar appears to be unable to set seeds. To the best of the breeders' knowledge would not be able to be a seed parent, but could be a pollen parent.

*Nectaries.*—Size: diminishingly small, less than 1 mm, color: yellow.

*Fragrance.*—No fragrance.

*Fruit production.*—No fruit production.

Resistance/susceptibility: None known in respect of plant/pest resistance/susceptibility.

Tolerance: Frost: some tolerance (survived temperature of −7° C.); drought: tolerant.

We claim:

1. A new and distinct plant, a cultivar of *Grevillea,* named *Grevillea* sp. 'Little Honey', as herein illustrated and described.

* * * * *